US00PP26847P3

(12) United States Plant Patent
Jacobs

(10) Patent No.: US PP26,847 P3
(45) Date of Patent: Jun. 21, 2016

(54) ***CHRYSANTHEMUM* PLANT NAMED 'ZANMUMAJES'**

(50) Latin Name: ***Chrysanthemum×morifolium* Ramat.**
Varietal Denomination: Zanmumajes

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chysanthemum Breeders Association Research B.V., Valkenburg (NL)

( * ) Notice: Subject to any disclaimer, the term of this patent is extended or adjusted under 35 U.S.C. 154(b) by 193 days.

(21) Appl. No.: 13/998,973

(22) Filed: Dec. 30, 2013

(65) Prior Publication Data

US 2015/0189811 P1 Jul. 2, 2015

(51) Int. Cl.
*A01H 5/02* (2006.01)

(52) U.S. Cl.
USPC ..... Plt./287

(58) Field of Classification Search
USPC ..... Plt./287
See application file for complete search history.

*Primary Examiner* — Keith Robinson
(74) *Attorney, Agent, or Firm* — Steptoe & Johnson LLP

(57) ABSTRACT

A *Chrysanthemum* plant named 'Zanmumajes' characterized by its small sized blooms with purple ray florets and prolific branching; natural season flowering date September 23-27 (week 39); blooming for a period of 4 weeks.

3 Drawing Sheets

Botanical designation: *Chrysanthemum×morifolium* Ramat.

Cultivar denomination: 'Zanmumajes'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmumajes'. 'Zanmumajes' is a product of a breeding and selection program for outdoor pot mums (garden mums) which had the objective of creating new cultivars with a double type inflorescence, a natural season flowering date around week 39, blooming for a period of 5 weeks. 'Zanmumajes' is a seedling resulting from a cross of the female parent id 28184 (not patented) with the male parent id 26513 (not patented). Plants of the new cultivar 'Zanmumajes' differ from its parent in inflorescence color; the inflorescences of the seedling are purple with a dark center, while they are two-tone pink in the female parent and dark pink in the male parent.

The new and distinct cultivar was discovered and selected as a flowering plant by Henricus Cornelius Maria Jacobs on a cultivated field in Rijsenhout, The Netherlands in 2005. The first act of asexual production of 'Zanmumajes' was accomplished when vegetative cuttings from the initial selection in 2005 were propagated further in a controlled environment in Rijsenhout, The Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *Chrysanthemum* (of about 18 weeks) is shown in the accompanying drawings, the color being as nearly true as possible with color photographs of this type.

DESCRIPTION OF THE INVENTION

Figure 1:
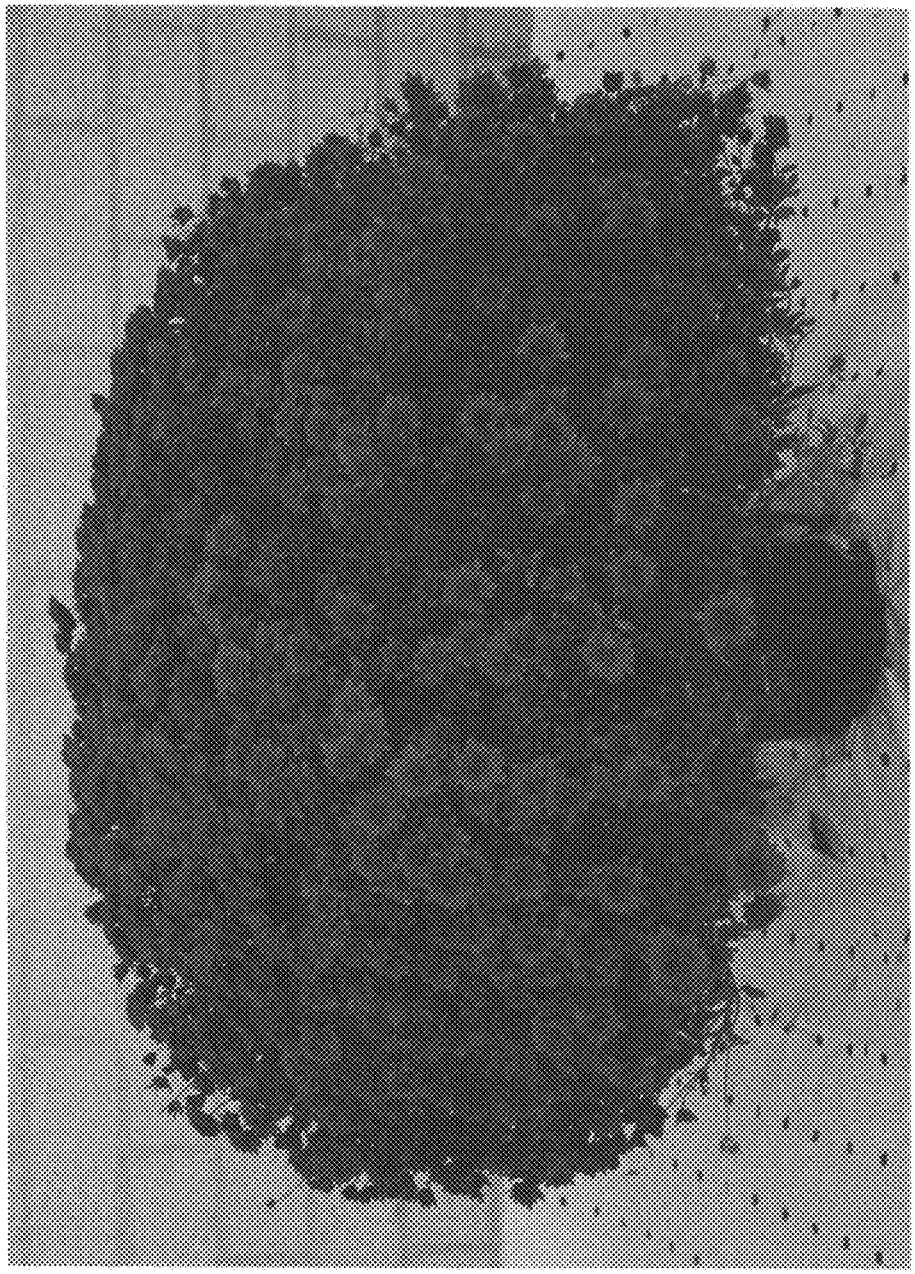
FIG. 1 shows a plant of the cultivar in full bloom.
Figure 2:
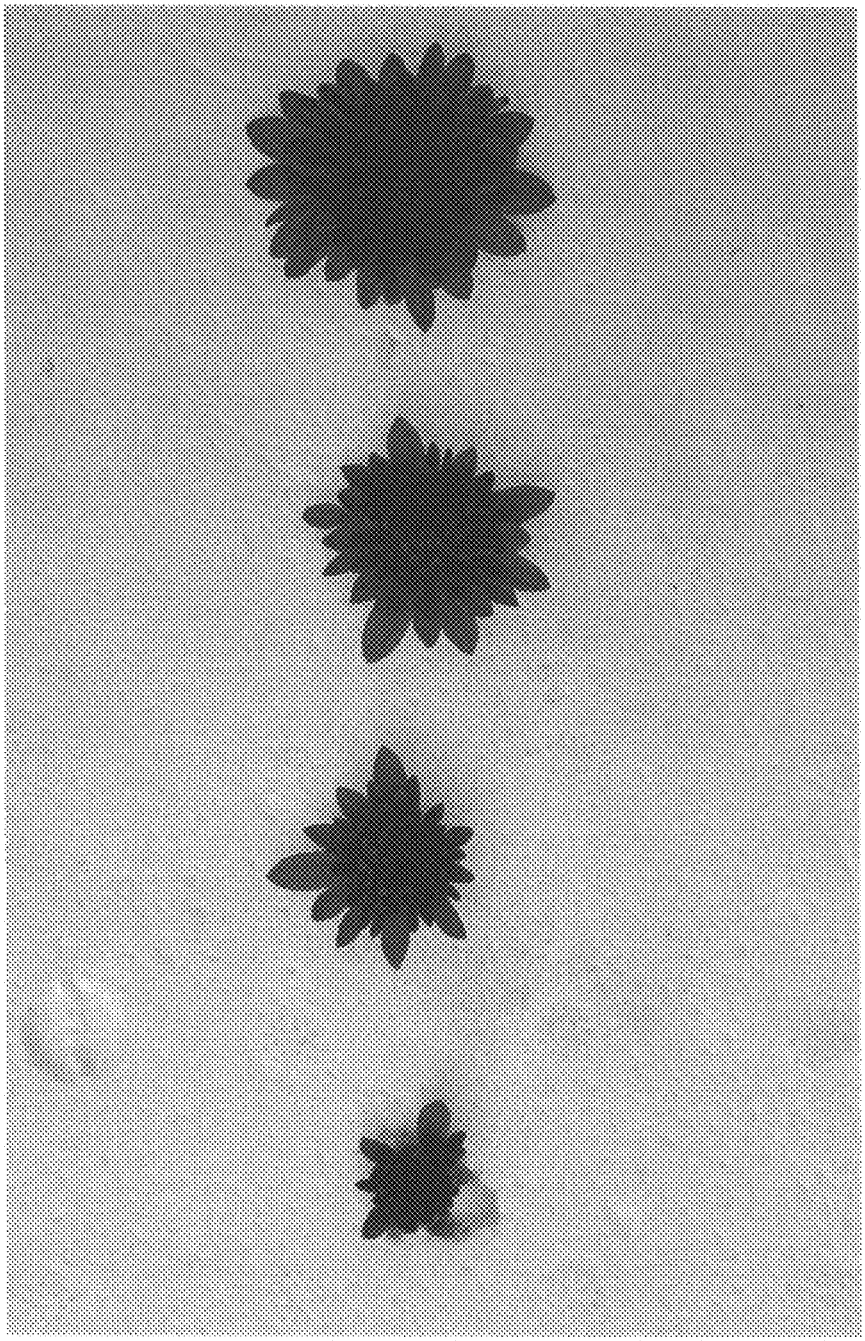
FIG. 2 shows the various stages of bloom of the new cultivar.
Figure 3:
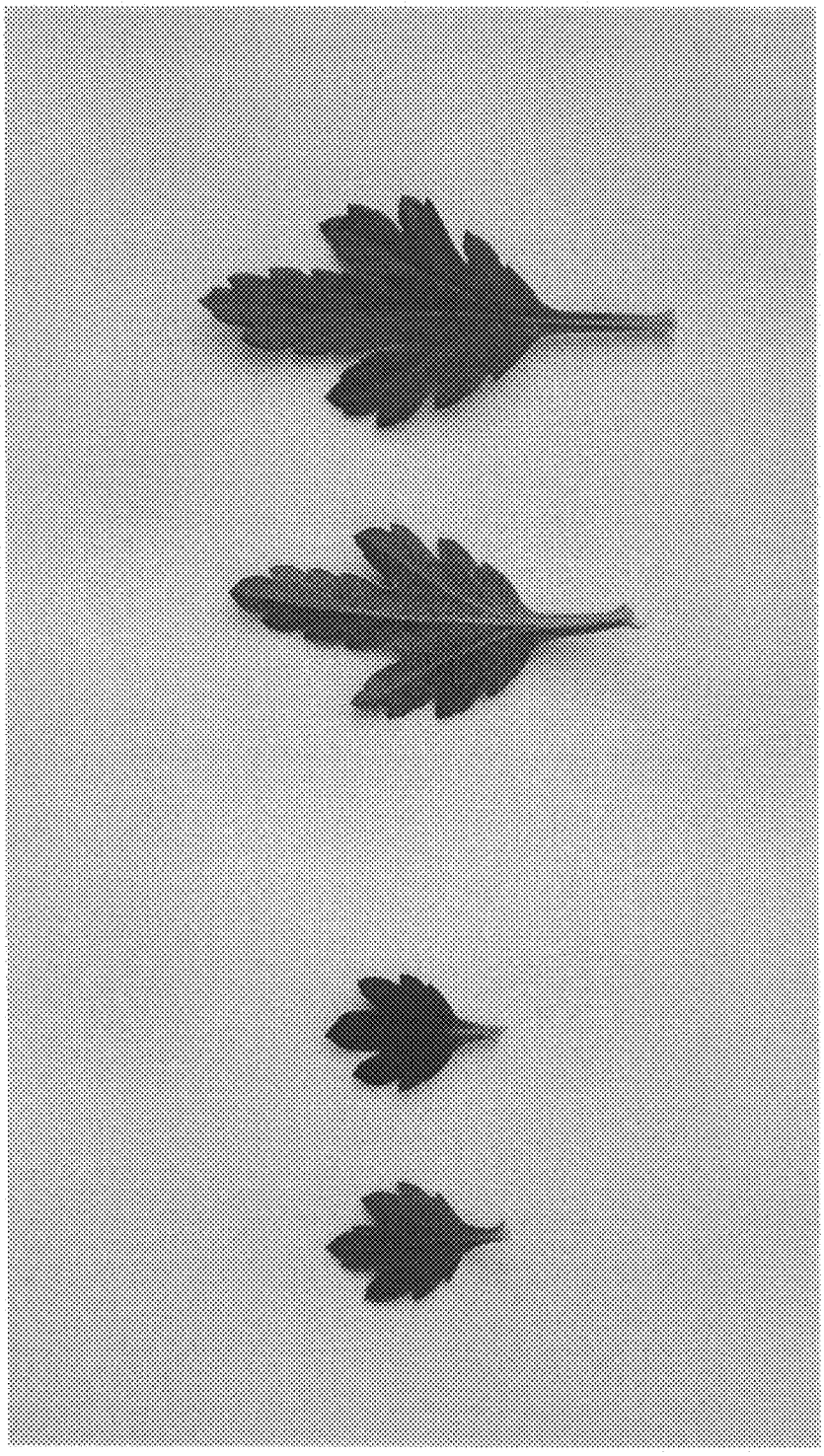
FIG. 3 shows the various stages of foliage of the new cultivar.

The observations and measurements were gathered from plants, in the period of 17 to 24 weeks of age, grown outdoor in Rijsenhout, The Netherlands, under natural day length and temperature and planted in week 23 in 2013 (with a warm summer), receiving drip irrigation. The natural blooming date of this crop was September 23-27 (week 39). The average height of the plants was 40 cm. No growth retardants were used. No tests were done on disease or insect resistance or susceptibility. No tests were done on cold or drought tolerance. This new variety produces small sized blooms with purple ray florets blooming for a period of 5 weeks. From the cultivars known to the inventor the most similar existing cultivar in comparison to 'Zanmumajes' is 'Venus' (U.S. Plant Pat. No. 14,378). When 'Venus' and 'Zanmumajes' are being compared the following differences are noticed (1). Inflorescence size. And (2). Natural season flower date. (1). Inflorescences of 'Venus' are larger than those of 'Zanmumajes'. (2). Plants of 'Venus' flower earlier in the season than those of 'Zanmumajes'.

The following is a description of the plant and characteristics that distinguish 'Zanmumajes' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmumajes'

| | |
|---|---|
| **Bud** | |
| Size: | Small; cross-section 3 mm, height 3 mm |
| Shape: | Round |
| Texture: | Pubescent |
| Outside color: | Greyed-green 191A |
| **Phyllaries** | |
| Number: | 18, arranged in 3 rows |
| Shape: | Elliptic |
| Apex: | Acute |
| Base: | Truncate |
| Margin: | Entire |
| Color: | Upper side: Green 137C<br>Lower side: Yellow-green 144C |
| Length and width: | 3 mm; 1.5 mm |
| Texture: | Pubescent |
| **Inflorescences** | |
| Type: | Double |
| Height: | 1 cm |
| Diameter: | 3 cm |
| Peduncle length: | 5.5-6.5cm |
| Peduncle color: | Green 143C |
| Peduncle diameter: | 1.5 mm |
| Peduncle texture: | Pubescent |
| Peduncle strength: | Weak |
| Number per branch: | About 7-8 inflorescences |
| Duration of flowering: | 4 weeks |
| Seeds: | Produced in small quantities, ovate, Greyed-brown 199A, length 1.5 mm, diameter 0.5 mm; texture: rough with ribs |
| Fragrance: | Faint chrysanthemum odor |
| **Color inflorescences** | |
| Center of inflorescence: | Immature stage: Greyed-purple 187B; Mature stage: Greyed-purple 187B |
| Color of upper side of ray florets: | Purple N77B |
| Color of lower side of ray florets: | Greyed Purple 186C |
| Tonality from distance: | A garden mum with small decorative purple blooms and a dark center |
| Color of ray florets after aging of the plant: | Greyed-purple 186C |
| **Ray florets** | |
| Type: | Ligulate |
| Texture: | Upper and lower side smooth |
| Number: | 90-100 |
| Shape: | elliptic |
| Apex: | pointed |
| Base: | attenuate |
| Cross-section: | flat |
| Longitudinal axis: | straight |
| Length of corolla tube: | 2 mm |
| Diameter corolla tube: | 0.8-1 mm |
| Ray floret margin: | Entire |
| Ray floret length: | 1-1.5 cm |
| Ray floret width: | 2-4 mm |
| Ratio length/width: | Medium |
| Disc florets | Absent |
| **Receptacle** | |
| Color: | Yellow-green 145D |
| Shape: | Domed raised |
| Height: | 3 mm |
| Diameter: | 2 mm |
| **Reproductive Organs** | |
| Androecium: | absent |
| Pollen: | absent |
| Gynoecium: | Present on ray florets |
| Style color: | Yellow-green 154C |
| Style length: | 4 mm |

TABLE 1-continued

Botanical Description of *Chrysanthemum* × *morifolium* Ramat. 'Zanmumajes'

| | |
|---|---|
| Stigma color: | Yellow 7A |
| Stigma width: | 1 mm |
| Ovary: | Enclosed in calyx; color: Yellow-green 149D |
| **Plant** | |
| Type: | Bushy |
| Growth habit: | Spherical shape |
| Growth rate: | Medium/Low |
| Height: | 40 cm |
| Width: | 50 cm |
| Stem color: | Greyed-brown 199A |
| Stem strength: | weak |
| Stem brittleness: | brittle |
| Stem anthocyanin coloration: | absent |
| Internode length: | 2-3 cm |
| Length of lateral branch: | From top to bottom 20-22 cm |
| Lateral branch color: | Green 138B |
| Lateral branch, attachment: | Weak |
| Lateral branch diameter: | 2 mm |
| Lateral branch texture: | Pubescent with ribs |
| Branching (average number of lateral branches): | Dense with 9 breaks after pinching |
| Natural season blooming date: | September 23-27 (week 39) in Rijsenhout, The Netherlands. |
| Roots - habits: | Fine, freely branching |
| Roots - color: | White 155D |
| **Foliage** | |
| Glossiness: | Leaf upper side: very weak<br>Leaf lower side: very weak |
| Leaf color: | Upper side: Green 138A<br>Lower side: Green 139C |
| Color midvein: | Upper side: Yellow-green 147D<br>Lower side: Yellow-green 148D |
| Size: | Small; length 2.5-4.5 cm, width 1.2-2.4 cm |
| Quantity (number per lateral branches): | 20-22 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Acute to truncate |
| Apex: | Mucronulate |
| Petiole attitude: | Moderately upwards |
| Petiole length: | 0.2-0.5 cm |
| Petiole diameter: | 1.5 mm |
| Petiole color: | Yellow-green 147D |
| Stipule: | Very small, about 8 mm. |

TABLE 2

Differences with the comparison variety, when grown under identical conditions

| | 'Zanmumajes' | 'Venus' |
|---|---|---|
| Inflorescence size | 3 cm | 5-5.5 cm |
| Natural season flower date | week 35 | week 39 |

I claim:

1. A new and distinct *Chrysanthemum* plant named 'Zanmumajes' as described and illustrated.

* * * * *